(12) United States Patent
Moriya

(10) Patent No.: US 11,160,749 B2
(45) Date of Patent: Nov. 2, 2021

(54) COSMETIC

(71) Applicant: SHIN-ETSU CHEMICAL CO., LTD., Tokyo (JP)

(72) Inventor: Hiroyuki Moriya, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/487,883

(22) PCT Filed: Feb. 9, 2018

(86) PCT No.: PCT/JP2018/004501
§ 371 (c)(1),
(2) Date: Aug. 22, 2019

(87) PCT Pub. No.: WO2018/189992
PCT Pub. Date: Oct. 18, 2018

(65) Prior Publication Data
US 2020/0246248 A1    Aug. 6, 2020

(30) Foreign Application Priority Data

Apr. 10, 2017 (JP) .............................. JP2017-077472

(51) Int. Cl.
*A61K 8/895* (2006.01)

(52) U.S. Cl.
CPC .......... *A61K 8/895* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 4,970,252 A | 11/1990 | Sakuta et al. | |
| 4,987,169 A | 1/1991 | Kuwata et al. | |
| 5,236,986 A | 8/1993 | Sakuta | |
| 2003/0199660 A1 | 10/2003 | Sakuta | |
| 2004/0234477 A1 | 11/2004 | Sakuta | |
| 2004/0253197 A1 | 12/2004 | Sakuta | |
| 2012/0312316 A1 | 12/2012 | Tomita | |
| 2017/0240677 A1* | 8/2017 | Akabane | ............ C08F 290/068 |
| 2017/0306184 A1 | 10/2017 | Nakayama | |

FOREIGN PATENT DOCUMENTS

| | | |
|---|---|---|
| EP | 2532348 A1 | 12/2012 |
| JP | S61-065809 A | 4/1986 |
| JP | H02-025411 A | 1/1990 |
| JP | H04-342513 A | 11/1992 |
| JP | H06-055897 B2 | 7/1994 |
| JP | H06-060286 B2 | 8/1994 |
| JP | H07-187954 A | 7/1995 |
| JP | H08-239308 A | 9/1996 |
| JP | H09-136813 A | 5/1997 |
| JP | 2631772 B2 | 7/1997 |
| JP | 2001-342255 A | 12/2001 |
| JP | 2004-269443 A | 9/2004 |
| JP | 2007-161600 A | 6/2007 |
| JP | 2009-185296 A | 8/2009 |
| JP | 2010-275512 A | 12/2010 |
| JP | 2012-072081 A | 4/2012 |
| JP | 2014-198678 A | 10/2014 |
| JP | WO2016035232 * | 3/2016 |
| JP | 2016-053010 A | 4/2016 |
| WO | 03/020828 A1 | 3/2003 |
| WO | 03/024413 A1 | 3/2003 |
| WO | 2011/096337 A1 | 8/2011 |
| WO | 2016059841 A1 | 4/2016 |

OTHER PUBLICATIONS

Dec. 14, 2020 Extended European Search Report issued in European Patent Application No. 18785038.3.
Oct. 23, 2019 Japanese Office Action issued in Japanese Patent Application No. 2017-77472.
Oct. 15, 2019 International Preliminary Report on Patentability issued in International Patent Application No. PCT/JP2018/004501.
Apr. 10, 2018 International Search Report issued in International Patent Application No. PCT/JP2018/004501.

* cited by examiner

*Primary Examiner* — Jennifer A Berrios
(74) *Attorney, Agent, or Firm* — Oliff PLC

(57) ABSTRACT

A cosmetic including an acryl silicone copolymer having a (meth)acrylic chain in the main chain and a structure containing at least a silicone macromonomer shown by the following general formula (1) as the monomer unit (the acryl silicone copolymer has a refractive index of 1.47 or more). A novel glossy cosmetic that is free from tautness or stiffness unlike previous silicone resin coatings, excellent in feeling of use, adherence, and flexibility, as well as good in effect for preventing color transfer.

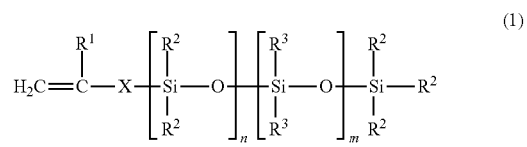

(1)

18 Claims, No Drawings

COSMETIC

TECHNICAL FIELD

The present invention relates to a cosmetic.

BACKGROUND ART

Previous make-up cosmetics have been troubled with secondary adhesion, for example, lipstick applied to lips is unsuccessfully transferred to a cup and so on. Foundations also have been troubled with secondary adhesion in which applied cosmetic unsuccessfully adheres to clothes. These phenomena, including unevenness of cosmetic caused by perspiration or sebum, are called make-up deterioration.

Accordingly, various products have been proposed by incorporating a volatile and/or nonvolatile silicone oil and hydrocarbon oil as make-up cosmetics that is less liable to cause secondary adhesion, that is, excellent in transfer resistance and less liable to cause make-up deterioration.

For example, Patent Document 1 discloses a make-up cosmetic containing an organic silicone resin with a specific structure, a volatile silicone oil, and powder, which has excellent effect of preventing make-up deterioration, is good in spreading, and gives refreshing feeling of use. However, this silicone resin forms a hard coating to cause tautness or stiffness, and sometimes causes dryness thereby.

Patent Document 2 discloses a cosmetic containing methylphenylpolysiloxane, in which the methylphenylpolysiloxane disposed on the surface gives gloss, good cosmetic sustainability, and smudge resistance. The methylphenylpolysiloxane is liquid, however, and is transferred after several eating and drinking to cause color transfer.

Patent Documents 3, 4, and 5 describe investigations of using a silicone-grafted acrylic polymer as a coating agent. Such a silicone-grafted acrylic polymer forms a coating with lower strength and have a trouble in secondary adhesion.

Patent Document 6 describes a silicone-grafted acrylic polymer that has monomer units derived from a long-chain alkyl monomer and a hydrophilic monomer. Although this polymer is improved in feeling, compatibility, and sliding properties, these properties are still insufficient.

Accordingly, a make-up cosmetic has been demanded which is less liable to cause secondary adhesion, good in adherence and flexibility of the coating, and excellent in feeling of use, containing a coating agent that makes a cosmetic film higher glossy to enhance the make-up effect.

CITATION LIST

Patent Literature

Patent Document 1: Japanese Unexamined Patent Application Publication No. S61-65809
Patent Document 2: International Patent Laid-Open Publication No. WO 2011-096337
Patent Document 3: Japanese Unexamined Patent Application Publication No. H07-187954
Patent Document 4: Japanese Unexamined Patent Application Publication No. H04-342513
Patent Document 5: Japanese Unexamined Patent Application Publication No. H02-25411
Patent Document 6: Japanese Unexamined Patent Application Publication No. 2012-072081

SUMMARY OF INVENTION

Technical Problem

The present invention was accomplished in view of the above-described problems. It is an object of the present invention to provide a novel glossy cosmetic that is free from tautness or stiffness unlike previous silicone resin coatings, excellent in feeling of use, adherence, and flexibility, as well as good in effect of preventing color transfer.

Solution to Problem

To solve the foregoing problems, the present invention provides a cosmetic comprising an acryl silicone copolymer having a (meth)acrylic chain in a main chain and a structure containing at least a silicone macromonomer shown by the following general formula (1) as a monomer unit (provided that the acryl silicone copolymer has a refractive index of 1.47 or more):

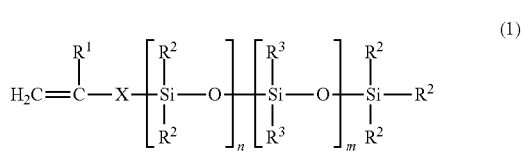

in the formula (1), X represents a divalent aromatic group having 6 to 12 carbon atoms or $-COOR^4-$, where $R^4$ represents a divalent aliphatic group optionally containing an oxygen atom bonded to Si; $R^1$ represents a hydrogen atom or a methyl group; each $R^2$ represents the same or different unsubstituted monovalent alkyl group having 1 to 6 carbon atoms; $R^3$ represents a phenyl group; n is an integer of 1 to 100, m is an integer of 1 to 100, and a component ratio n/m is 1/2 to 4/1.

The cosmetic like this is free from tautness or stiffness unlike previous silicone resin coatings, excellent in feeling of use, adherence, and flexibility, as well as good in effect for preventing color transfer.

It is preferable that the acryl silicone copolymer contain an alicyclic (meth)acrylic monomer as a monomer unit.

The cosmetic like this is further improved in gloss, resistance to color transfer, and solubility to a volatile organic oil.

It is preferable that the acryl silicone copolymer contain 30 to 70 mass % of the silicone macromonomer shown by the general formula (1) as a monomer unit and 30 to 70 mass % of the alicyclic (meth)acrylic monomer as a monomer unit.

The cosmetic like this successfully combines higher gloss, feeling of use, adherence, flexibility, resistance to color transfer, and solubility to a volatile organic oil.

It is preferable that the acryl silicone copolymer be a copolymer that is free from causing precipitation or separation at 25° C. from a mixture of the acryl silicone copolymer with a volatile silicone oil or a volatile organic oil in a mass ratio of 7:3.

The cosmetic like this is particularly excellent in solubility to a volatile silicone oil or a volatile organic oil.

It is preferable that a volatile silicone oil or a volatile organic oil be contained in addition to the acryl silicone copolymer.

The cosmetic like this is further improved in feeling of use.

It is preferable that the cosmetic be a make-up cosmetic.

As described above, the inventive cosmetic can be favorably used particularly as a make-up cosmetics.

Advantageous Effects of Invention

The acryl silicone copolymer used for the present invention is soluble in wide variety of oils used for cosmetics, such as a volatile silicone oil and a volatile organic oil, and provides higher refractive index of 1.47 or more, thereby making it possible to make a cosmetic, particularly a make-up cosmetic, glossy and to form a coating that is free from sticky touch. Additionally, the cosmetic containing the acryl silicone copolymer is free from tautness or stiffness, excellent in feeling of use, adherence, and flexibility, as well as good in effect for preventing color transfer.

DESCRIPTION OF EMBODIMENTS

Hereinafter, the present invention will be described in more detail.

As described above, a novel glossy cosmetic has been demanded which is free from tautness or stiffness unlike previous silicone resin coatings, excellent in feeling of use, adherence, and flexibility, as well as good in effect for preventing color transfer.

The present inventors have diligently investigated to achieve the above objects to find that the cosmetic, containing the an acryl silicone copolymer having a monomer unit derived from a silicone macromonomer that contains a phenyl group and an unsubstituted monovalent alkyl group having 1 to 6 carbon atoms in a specific ratio, comes to be glossy, free from tautness or stiffness, and excellent in feeling of use, adherence, and flexibility, as well as good in effect of preventing color transfer. The present inventors have also found that the acryl silicone copolymer is particularly preferable to contain a monomer unit derived from an alicyclic (meth)acrylic monomer in order to further enhance the effects described above; thereby bringing the present invention to completion. Such an acryl silicone copolymer has never actually been synthesized nor added to a cosmetic.

That is, the present invention is a cosmetic that contains an acryl silicone copolymer having a (meth)acrylic chain in the main chain, with the structure containing at least a silicone macromonomer shown by the following general formula (1) as the monomer unit (provided that the acryl silicone copolymer has a refractive index of 1.47 or more):

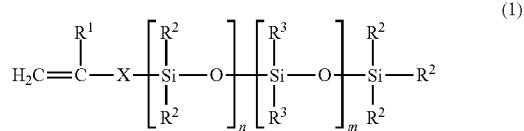
(1)

in the formula (1), X represents a divalent aromatic group having 6 to 12 carbon atoms or —COOR$^4$—, where R$^4$ represents a divalent aliphatic group and may contain an oxygen atom bonded to Si; R$^1$ represents a hydrogen atom or a methyl group; each R$^2$ may be the same or different and represents an unsubstituted monovalent alkyl group having 1 to 6 carbon atoms; R$^3$ represents a phenyl group; n is an integer of 1 to 100, m is an integer of 1 to 100, and a component ratio n/m is 1/2 to 4/1.

Hereinafter, the present invention will be described in more detail, but the present invention is not limited thereto.

The silicone macromonomer is shown by the general formula (1):

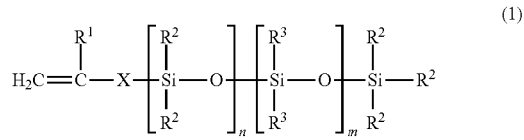
(1)

in the formula (1), X represents a divalent aromatic group having 6 to 12 carbon atoms or —COOR$^4$—, where R$^4$ represents a divalent aliphatic group optionally containing an oxygen atom bonded to Si; R$^1$ represents a hydrogen atom or a methyl group; each R$^2$ represents the same or different unsubstituted monovalent alkyl group having 1 to 6 carbon atoms; R$^3$ represents a phenyl group; n is an integer of 1 to 100, m is an integer of 1 to 100, and a component ratio n/m is 1/2 to 4/1.

In the silicone macromonomer shown by the general formula (1), R$^1$ is a hydrogen atom or a methyl group, preferably a methyl group.

Each R$^2$ represents the same or different unsubstituted monovalent alkyl group having 1 to 6 carbon atoms; preferably a methyl group, an ethyl group, a propyl group, a butyl group, a pentyl group, or a hexyl group; more preferably a methyl group.

R$^3$ is a phenyl group. The silicone macromonomer shown by the general formula (1) contains a phenyl group(s) in order to make the resin glossy.

X is a divalent aromatic group having 6 to 12 carbon atoms or —COOR$^4$—, preferably a divalent aromatic group having 6 to 8 carbon atoms or —COOR$^4$—. Illustrative examples of the divalent aromatic group include a phenylene group, a tolylene group, a xylylene group, and mesitylene group, in which a phenylene group is preferable. In —COOR$^4$—, R$^4$ is a divalent aliphatic group optionally containing an oxygen atom bonded to Si, and the carbonyl group is bonded to a carbon atom in the main chain of the copolymer. R$^4$ is —(CH$_2$)$_a$—, for example, wherein "a" is an integer of 1 to 9, preferably an integer of 2 to 7, more preferably an integer of 3 to 5.

In the above formula, n is in 1 to 100, preferably 1 to 80; m is in 1 to 100, preferably 1 to 80; and the component ratio n/m is in a range of 1/2 to 4/1, preferably 1/2 to 3/1. It is difficult to actually synthesize a silicone macromonomer in which n/m is less than 1/2. In case of n/m being more than 4/1, the refractive index decreases, and the formulated cosmetic fails to have sufficient gloss to lower the make-up effect. Additionally, the coating is lowered in flexibility and feeling, and the secondary adhesion is also lowered.

Acryl Silicone Copolymer

The acryl silicone copolymer has a refractive index of 1.47 or more, preferably 1.48 or more and 1.54 or less. In case of refractive index being less than 1.47, the cosmetic fails to have sufficient gloss to lower the make-up effect.

The acryl silicone copolymer preferably contains an alicyclic (meth)acrylic monomer as the monomer unit. Illustrative examples of the alicyclic (meth)acrylic monomer include adamantyl (meth)acrylate, isobornyl (meth)acrylate, dicyclopentenyl (meth)acrylate, dicyclopentenyloxyethyl (meth)acrylate, and dicyclopentanyl (meth)acrylate; preferable example thereof are adamantyl (meth)acrylate, isobornyl (meth)acrylate, dicyclopentenyl (meth)acrylate, and dicyclopentanyl (meth)acrylate; more preferably adamantyl (meth)acrylate and dicyclopentanyl (meth)acrylate. The alicyclic (meth)acrylic monomer has higher refractive index and can give higher gloss thereby. Due to higher phenyl content, the acryl silicone macromonomer of the formula (1) tends to lower the solubility to a volatile silicone oil or a volatile organic oil. Accordingly, an introduction of the monomer unit derived from an aliphatic (meth)acrylic monomer can improve the solubility. Additionally, adamantyl (meth)acrylate and dicyclopentanyl (meth)acrylate each have a relatively high glass transition temperature, making it possible to form a strong coating to improve the secondary adhesion.

The acryl silicone copolymer preferably contains 30 to 70 mass % of the silicone macromonomer shown by the general formula (1) as the monomer unit and 30 to 70 mass % of the alicyclic (meth)acrylic monomer as the monomer unit. The content of silicone macromonomer shown by the general formula (1) is preferably 40 to 60 mass %, and the content of alicyclic (meth)acrylic monomer is preferably 30 to 60 mass %.

The acryl silicone copolymer for the present invention is additionally composed of other monomer unit component that has a radical polymerizable vinyl group. Illustrative examples of such a vinyl monomer include lower alkyl (meth)acrylates such as methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-hexyl (meth)acrylate, and cyclohexyl (meth)acrylate; higher alkyl (meth)acrylate such as 2-ethyl-cylohexyl (meth)acrylate, octyl (meth)acrylate, lauryl (meth)acrylate, and stearyl (meth)acrylate; vinyl fatty acid esters such as vinyl acetate, vinyl propionate, vinyl butyrate, vinyl caproate, vinyl 2-ethylhexanoate, vinyl laurate, and vinyl stearate; aromatic monomers such as styrene, vinyltoluene, benzyl (meth)acrylate, and phenoxyethyl (meth)acrylate; amide group-containing vinyl type monomers such as (meth)acrylamide, N-methylol (meth)acrylamide, N-methoxymethyl (meth)acrylamide, isobutoxymethoxy (meth)acrylamide, N,N-dimethyl (meth)acrylamide, vinyl pyrrolidone, and N-vinyl acetamide; hydroxy group-containing vinyl type monomers such as hydroxyethyl (meth)acrylate, hydroxypropyl (meth)acrylate, glyceryl (meth)acrylate, and hydroxyethyl acrylamide; ether bond-containing vinyl type monomers such as tetrahydrofurfuryl (meth)acrylate, butoxyethyl (meth)acrylate, ethoxydiethyleneglycol (meth)acrylate, polyethylene glycol (meth)acrylate, polypropylene glycol mono(meth)acrylate, hydroxybutyl vinyl ether, cetyl vinyl ether, and 2-ethylhexyl vinyl ether; as well as glycidyl (meth)acrylate, (meth)allyl glycidyl ether, and methacryloyloxyethyl isocyanate.

Additionally, a multifunctional vinyl monomers are also usable, and illustrative examples thereof include trimethylolpropane tri(meth)acrylate, pentaerythritol tri(meth)acrylate, ethylenglycol di(meth)acrylate, tetraethyleneglycol di(meth)acrylate, polyethyleneglycol di(meth)acrylate, 1,4-butanediol di(meth)acrylate, 1,6-hexanediol di(meth)acrylate, neopentylglycol di(meth)acrylate, trimethylolpropane trioxyethyl (meth)acrylate, tris(2-hydroxyethyl)isocyanurate di(meth)acrylate, tris(2-hydroxyethyl)isocyanurate tri(meth)acrylate, and unsaturated group-containing silicone compounds such as polydimethylsiloxane terminated with a styryl group(s).

The acryl silicone copolymer for the present invention can be produced by polymerization of the monomers described above under the presence of a radical polymerization initiator such as benzoyl peroxide, laouroyl peroxide, and azobis(isobutyronitrile). Any polymerization method can be applied including solution polymerization, emulsion polymerization, suspension polymerization, and bulk polymerization. Among them, solution polymerization is a preferable method because it makes easy to appropriately adjust the weight average molecular weight of the copolymer and dispersion of graph in gel permeation chromatography (GPC) in determination of a weight average molecular weight obtained thereby. In this polymerization, illustrative examples of usable solvent include aliphatic organic solvents such as pentane, hexane, decane, dodecane, hexadecane, and octadecane; aromatic organic solvents such as benzene, toluene, and xylene; alcoholic organic solvents such as methanol, ethanol, propanol, butanol, hexanol, and decanol; halogenated organic solvents such as chloroform and carbon tetrachloride; ketone organic solvents such as acetone and methyl ethyl ketone. The polymerization reaction may be performed in such an organic solvent.

Thus produced acryl silicone copolymer preferably has a weight average molecular weight of 700 to 500,000, particularly 5000 to 400,000, still more preferably 8000 to 200,000 in terms of polystyrene in GPC.

Illustrative examples of the copolymer that can be produced as described above include a copolymer produced by copolymerization of a silicone macromonomer shown by the general formula (1) and an alicyclic (meth)acrylic monomer as well as a copolymer produced by copolymerization of a silicone macromonomer shown by the general formula (1), an alicyclic (meth)acrylic monomer, and (an)other monomer(s). The cosmetic containing such a copolymer is glossy, excellent in transfer resistance, less liable to cause make-up deterioration, good in stability and usability, and free from smudging.

The acryl silicone copolymer for the present invention is preferably a copolymer that is not precipitated nor separated at 25° C. when it is mixed with a volatile silicone oil or a volatile organic oil in a mass ratio of 7:3. Such a condition can be satisfied by the composition of acryl silicone copolymer described above.

In the present invention, it is preferable to contain a volatile silicone oil or a volatile organic oil in addition to the acryl silicone copolymer. They can be used alone or a mixture thereof, and illustrative examples of the volatile silicone oil include dimethylpolysiloxanes (dimer, trimer, tetramer, pentamer), caprylyl methicone, octamethylcyclotetrasiloxane, decamethylcyclopentasiloxane, dodecamethylcyclohaxasiloxane, tetramethyltetrahydrogencyclotetrasiloxane, tris(trimethylsiloxy)methylsilane, and tetrakis(trimethylsiloxy)silane. Illustrative examples of the volatile organic solvent include hydrocarbon oils such as α-olefin oligomer, light isoparaffin, isododecane, light liquid isoparaffin, and butyl acetate. Preferable examples are dimethylpolysiloxanes (tetramer, pentamer), caprylyl methicone, decamethylcyclopentasiloxane, dodecamethylcyclohaxasiloxane, tris(trimethylsiloxy)methylsilane, tetrakis(trimethylsiloxy)silane, light isoparaffin, isododecane, light liquid isoparaffin, and butyl acetate. The amount of these volatile oils to be blended is 1 to 98 mass %, preferably 1 to 50 mass %, more preferably 3 to 30 mass % relative to the whole cosmetic.

In the present invention, it is possible to contain an oil material that is allowable for cosmetics in addition to the volatile oil described above. Illustrative examples of such an oil material include one or two kinds of silicone oil(s), hydrocarbon oil(s), higher fatty acid, polar oils such as ester oil(s) and natural animal and vegetable oils, semisynthetic oil(s), and/or fluorinated oil(s).

Illustrative examples of the silicone oil include linear or branched organopolysiloxane having low viscosity to high viscosity such as nonvolatile dimethylpolysiloxane, phenyltrimethicone, methylphenylpolysiloxane, methylhexylpolysiloxane, methylhydrogenpolysiloxane, and dimethylsiloxane/methylphenylsiloxane copolymer; tetramethyltetraphenylcyclotetrasiloxane, amino modified organopolysiloxane; silicone rubbers such as highly polymerized gummy dimethylpolysiloxane, gummy amino modified organopolysiloxane, and a gummy dimethylsiloxane/methylphenylsiloxane copolymer; a solution of silicone gum or silicone rubber in cyclic siloxane, trimethylsiloxy silicic acid, a solution of trimethylsiloxy silicic acid in cyclic organopolysiloxane, higher alkoxy-modified organopolysiloxanes such as stearoxy silicone, higher fatty acid-modified organopolysiloxane, alkyl-modified organopolysiloxane, long chain alkyl-modified organopolysiloxane, fluorine-modified organopolysiloxane, a silicone resin, and a solution of silicone resin.

Illustrative examples of the hydrocarbon oil include non-volatile ones such as ozocerite, squalane, synthetic squalane, vegetable squalane, squalene, ceresin, paraffin, paraffin wax, polyethylene wax, polyethylene/polypropylene wax, an ethylene/propylene/styrene copolymer, a butylene/propylene/styrene copolymer, liquid paraffin, liquid isoparaffin, pristane, polyisobutylene, hydrogenated polyisobutene, microcrystalline wax, and vaseline.

Illustrative examples of the higher fatty acid include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid. Illustrative examples of the higher alcohol include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyl tetradecynol, cholesterol, phytosterol, POE cholesteryl ether, monostearyl glycerin ether (batyl alcohol), and monooleyl glyceryl ether (selachyl alcohol).

Illustrative examples of the ester oil include diisobutyl adipate, 2-hexyldecyl adipate, 2-heptylundecyl adipate, an N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dioctanoate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, isopropyl lauroylsarcosinate ester, and diisostearyl malate. Illustrative examples of the glyceride oil include acetoglyceryl, glyceryl triisooctanoate, glyceryl triisostearate, glyceryl triisopalmitate, glyceryl monostearate, glyceryl di-2-heptylundecanoate, glyceryl trimyristate, and diglyceryl myristate isostearate.

Illustrative examples of the natural animal and vegetable oils and semisynthetic oils include avocado oil, linseed oil, almond oil, insects wax, perilla oil, olive oil, cacao butter, kapok wax, kaya oil, carnauba wax, lever oil, candellila wax, purified candellila wax, beef tallow, neats-foot oil, beef bone fat, cured beef tallow, apricot kernel oil, whale wax, hydrogenated oil, wheat germ oil, sesame oil, rice germ oil, rice bran oil, sugarcane wax, sasanqua oil, safflower oil, Shea butter, Chinese tung oil, cinnamon oil, jojoba wax, squalane, squalene, shellac wax, turtle oil, soybean oil, tea seed oil, camellia oil, evening primrose oil, corn oil, pig fat, rapeseed oil, Japanese tung oil, bran wax, germ oil, horse fat, persic oil, palm oil, palm kernel oil, castor oil, cured castor oil, methyl ester of castor oil fatty acid, sunflower oil, grape seed oil, bayberry wax, jojoba oil, hydrogenated jojoba oil, macadamia nut oil, bees wax, mink oil, meadowfoam seed oil, cotton seed oil, cotton wax, Japan wax, Japan wax kernel oil, montan wax, coconut oil, cured coconut oil, tri-coconut fatty acid glyceride, mutton tallow, peanut oil, lanolin, liquid lanolin, reduced lanolin, lanolin alcohol, hard lanolin, lanolin acetate, lanolin alcohol acetate, isopropyl lanolin fatty acid, POE lanolin alcohol ether, POE lanolin alcohol acetate, polyethylene glycol lanolin fatty acid, POE hydrogenated lanolin alcohol ether, and an egg-yolk oil. Meanwhile, POE means polyoxyethylene.

Illustrative examples of the fluorinated oil material include perfluoro polyether, perfluoro decalin, and perfluoro octane.

The amount of the oil material that is allowable for cosmetics other than the volatile oil is dependent on the form of the cosmetic; but it is favorable to be in the range of 1 to 98 mass %, preferably 1 to 50 mass % relative to the whole cosmetic.

In the present invention, one or two or more kinds of ultraviolet light absorbing component(s) may be additionally contained. This allows the inventive cosmetic to absorb ultraviolet not only to have favorable feeling of use as well as excellent usability and durability. The ultraviolet light absorbing component includes an UV-absorber and an UV-scattering agent. Illustrative examples of the UV-absorber include a benzoic acid UV-absorber such as para-amino benzoic acid; an anthranilic acid UV-absorber such as methyl anthranilate; a salicylic acid UV-absorber such as methyl salicylate; a cinnamic acid UV-absorber such as octyl para-methoxy cinnamate; a benzophenone UV-absorber such as 2,4-dihydroxybenzophenone; a urocanic acid UV-absorber such as ethyl urocanate; a dibenzoylmethane UV-absorber such as 4-t-butyl-4'-methoxy-dibenzoylmethane. It is also possible to use silicone derivatives having an UV-absorbing functional group described above. Illustrative examples of the UV absorbing-scattering agent include particles that absorbs and scatters ultraviolet light such as titanium oxide microparticles, microparticles of titanium oxide containing iron, zinc oxide microparticles, cerium oxide microparticles, and a composite material thereof. Among them, a cinnamic acid UV-absorber, a dibenzoylmethane UV-absorber, titanium oxide, and zinc oxide are preferable.

In the present invention, water may be blended in accordance with the object.

In the present invention, one or two or more kinds of surfactant may be additionally contained. The inventive cosmetic is allowed to be particularly excellent in usability by blending surfactant in accordance with the object. The surfactant includes anionic, cationic, nonionic, and amphoteric surfactant. The inventive cosmetic can employ any surfactant that is used for ordinal cosmetics, which is not particularly limited.

Illustrative examples of the anionic surfactant include fatty acid soap such as sodium stearate and triethanolamine palmitate, alkyl ether carboxylic acid and a slat thereof, a condensation salt of amino acid and fatty acid, an alkane sulfonate salt, an alkene sulfonate salt, a sulfonate salt of fatty acid ester, a sulfonate salt of fatty acid amide, a sulfonate salt of formalin condensate, an alkyl sulfate ester salt, a sulfate ester salt of secondary higher alcohol, a sulfate ester salt of alkyl and allyl ether, a sulfate salt of fatty acid ester, a sulfate ester salt of fatty acid alkylolamide, a sulfate ester salt of Turkey red oil, an alkyl phosphate salt, an ether phosphate salt, an alkyl ally ether phosphate salt, an amide phosphate salt, an N-acyl lactate salt, an N-acylsarcosinate salt, and an N-acylamino acid activator. Illustrative examples of the cationic surfactant include an alkyl amine salt, an amine salt such as a fatty acid derivative of polyamine or a fatty acid derivative aminoalcohol, an alkyl quaternary ammonium salt, an aromatic quaternary ammonium salt, a pyridinium salt, and an imidazolium salt.

Illustrative examples of the nonionic surfactant include sorbitan fatty acid ester, glycerin fatty acid ester, polyglycerin fatty acid ester, propylene glycol fatty acid ester, polyethylene glycol fatty acid ester, sucrose fatty acid ester, methyl glucoside fatty acid ester, alkyl polyglucoside, polyoxyethylene alkyl ether, polyoxypropylene alkyl ether, polyoxyethylene alkyl phenyl ether, polyoxyethylene fatty acid ester, polyoxyethylene sorbitan fatty acid ester, polyoxyethyelene sorbitol fatty acid ester, polyoxyethylene glycerin fatty acid ester, polyoxyethylene propylene glycol fatty acid ester, polyoxyethylene castor oil, polyoxyethylene hard castor oil, polyoxyethylene phytostanol ether, polyoxyethylene phytosterol ether, polyoxyethylene cholestanol ether, polyoxyethylene cholesteryl ether, linear or branched polyoxyalkylene-modified organopolysiloxane, linear or branched organopolysiloxane co-modified with polyoxyalkylene and alkyl, linear or branched polyglycerin-modified organopolysiloxane, linear or branched organopolysiloxane co-modified with polyglycerin and alkyl, alkanol amide, sugar ether, and sugar amide.

Illustrative examples of the amphoteric surfactant include betaine, an aminocarboxylic acid salt, an imidazoline derivative, and an amide amine type.

Among these surfactants, preferable surfactants include linear or branched organopolysiloxane having a polyoxyethylene chain in the molecule, linear or branched organopolysiloxane having a polyglycerin chain in the molecule, and surfactants of these organopolysiloxane co-modified with alkyl. The commercial products thereof include KF-6011, KF-6011P, KF-6043, KF-6012, KF-6013, KF-6015, KF-6016, KF-6017, KF-6028, KF-6028P, KF-6038, KF-6100, KF-6104, and KF-6105 (all of which are manufactured by Shin-Etsu Chemical Co., Ltd.), but are not limited thereto. The surfactant preferably has HLB of 2 to 10. The amount to be blended is preferably 0.1 to 20 mass %, particularly 0.2 to 10 mass % relative to the whole cosmetic.

In the present invention, one or two or more kinds of powder may be contained. Any powder may be used if it is usable for ordinary cosmetics regardless of its form (spherical, needle-like, plate-like, etc.), its particle diameter (fumed, microparticle, pigment-class, etc.), and its particle structure (porous, non-porous, etc.). Illustrative examples thereof include inorganic powder, organic powder, surfactant metal salt powder, and coloring agents such as color pigment, pearl pigment, tar dye, metal powder pigment, natural pigment, and dyes.

Illustrative examples of the inorganic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, anhydrous silicic acid, aluminum silicate, magnesium silicate, aluminum magnesium silicate, calcium silicate, barium silicate, strontium silicate, a metal tungstate salt, hydroxy apatite, vermiculite, higilite, bentonite, montomorillonite, hectorite, zeolite, ceramics powder, dibasic calcium phosphate, alumina, aluminum hydroxide, boron nitride, silica, and silica silylate.

Illustrative examples of the organic powder include polyamide powder, polyacrylic acid/acrylic ester powder, polyester powder, polyethylene powder, polypropylene powder, polystyrene powder, polyurethane, bezoguanamine powder, polymethyl benzoguanamine powder, tetrafluoroethylene powder, polymethyl methacrylate powder, cellulose, silk powder, nylon powder, 12 nylon, 6 nylon, crosslinked spherical dimethylpolysiloxane microparticles having a structure of crosslinked dimethylpolysiloxane, crosslinked spherical polymethylsilsesquioxane microparticles, crosslinked spherical organopolysiloxane rubber microparticles with the surface being coated with polymethylsilsesquioxane particles, hydrophobic silica, styrene/acrylic acid copolymer, divinyl benzene/styrene copolymer, a vinyl resin, an urea resin, a phenolic resin, a fluorinated resin, a silicone resin, an acrylic resin, a melamine resin, an epoxy resin, a polycarbonate resin, fine crystalline fiber powder, starch powder, powder of starch derivative of fatty acid, and lauroyl lysine.

Illustrative examples of the surfactant metal salt powder (metal soap) include zinc undecylate, aluminum isostearate, zinc stearate, aluminum stearate, calcium stearate, magnesium stearate, zinc myristate, magnesium myristate, zinc cetylphosphate, calcium cetylphosphate, sodium zinc cetylphosphate, zinc palmitate, aluminum palmitate, and zinc laurate.

Illustrative examples of the color pigment include inorganic red pigment such as iron oxide, iron hydroxide, and iron titanate; an inorganic brown pigment such as γ-iron oxide; inorganic yellow pigment such as yellow iron oxide and yellow earth; inorganic black pigment such as black iron oxide and carbon black; inorganic purple pigment such as manganese violet and cobalt violet; inorganic green pigment such as chromium hydroxide, chromium oxide, cobalt oxide, and cobalt titanate; inorganic blue pigment such as Prussian blue and ultramarine blue; a laked tar dye; a laked natural dye; and synthetic resin powder obtained by hybridization of these powders.

Illustrative examples of the pearl pigment include muscovite coated with titanium oxide, mica coated with titanium oxide, oxychloro bismuth, oxychloro bismuth coated with titanium oxide, a talc coated with titanium oxide, a fish scale foil, and color mica coated with titanium oxide. Illustrative examples of the metal powder pigment include aluminum powder, copper powder, and stainless powder.

Illustrative examples of the tar dye include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207. Illustrative examples of the natural dye includes powder selected from carminic acid, laccaic acid, carthamin, brazilin, and crocin.

Among these powders, preferable ones for the present invention include crosslinked spherical dimethylpolysiloxane microparticles having a structure of at least partly crosslinked dimethylpolysiloxane, crosslinked spherical polymethylsilsesquioxane microparticles, crosslinked spherical polysiloxane rubber microparticles with the surface being coated with polymethylsilsesquioxane particles, crosslinked spherical diphenylpolysiloxane rubber microparticles with the surface being coated with polymethylsilsesquioxane particles, and hydrophobic silica; powder and coloring agents containing a fluorinated group are also usable. The commercial products thereof include KMP- 590, KSP-100, KSP-101, KSP-102, KSP-105, and KSP-300 (all of which are manufactured by Shin-Etsu Chemical Co., Ltd.).

These powders are usable as a composite thereof or after being treated with general oil material, silicone oil, a fluorine compound, and/or surfactant. They may be previously subjected to surface treatment such as treatment with a fluorine compound, treatment with a silicone resin, treatment for pendant, treatment with a silane coupling agent, treatment with a titanate coupling agent, treatment with oil material, treatment with N-acylated lysine, treatment with polyacrylic acid, treatment with metal soap, treatment with amino acid, treatment with an inorganic compound, plasma treatment, and mechanochemical treatment. In accordance with needs, one or two or more kinds of them may be used. The amount of the powder to be added is preferably in a range of 99 mass % or less relative to the whole cosmetic. In particular, the amount is favorable in a range of 80 to 99 mass % relative to the whole cosmetic in case of powder cosmetic.

In the present invention, it is possible to contain one or two or more kinds of compound(s) each having an alcoholic hydroxy group in the molecular structure. Illustrative examples of such a compound include lower alcohol such as ethanol and isopropanol; sugar alcohol such as sorbitol and maltose; sterol such as cholesterol, sitosterol, phytosterol, and lanosterol; and polyvalent alcohol such as butylene glycol, propylene glycol, dibutylene glycol, and pentylene glycol, in which water soluble monovalent alcohol and water soluble polyvalent alcohol are generally used in many cases. The cosmetic favorably contains the compound having an alcoholic hydroxy group in the molecular structure in an amount of 98 mass % or less relative to the whole cosmetic.

In the present invention, it is also possible to contain a composition composed of liquid oil material and one or two or more kinds of crosslinked organopolysiloxane polymer(s) without having a hydrophilic group. The crosslinked organopolysiloxane polymer can be obtained by reaction of alkylhydrogenpolysiloxane and a crosslinking agent that has a reactive vinyl type unsaturated group(s) at the terminal of the molecular chain. Illustrative examples of the alkylhydrogenpolysiloxane include linear or partially branched methylhydrogenpolysiloxane, methylhydrogenpolysiloxane in which an alkyl group with 6 to 20 carbon atoms is grafted, etc. Each of these molecules has to contain two or more hydrogen atoms that are bonded to silicon atom(s) in average. The crosslinking agent is exemplified by a molecule having two or more vinyl type reaction moieties, such as methylvinylpolysiloxane and α,ω-alkenyldiene. Illustrative examples thereof include compositions described in JP 1925781, JP 1932769, WO 03/24413A1, and JP 2009-185296A. This crosslinked methylpolysiloxane is swollen with larger weight of oil, for example, low viscosity silicone with the viscosity of 0.65 to 100.0 mm$^2$/second (at 25° C.), hydrocarbon oil such as liquid paraffin, squalane, and isododecane, glyceride oil such as trioctanoin, as well as ester oil. Illustrative examples of the commercially products of these crosslinked organopolysiloxane include KSG-15, KSG-16, KSG-18, KSG-1610, and USG-103, which are pastes mixed with silicone oil; USG-106, KSG-41, KSG-42, KSG-43, KSG-44, and KSG-810, which are pastes mixed with hydrocarbon oil or triglyceride oil (all of which are manufactured by Shin-Etsu Chemical Co., Ltd.), but not particularly limited thereto. The composition composed of liquid oil material and crosslinked organopolysiloxane without having a hydrophilic group is preferably blended in an amount of 0.1 to 50 mass %, more preferably 1 to 30 mass % relative to the whole amount of the cosmetic.

In the present invention, it is also possible to contain a composition composed of liquid oil material and one or two or more kinds of crosslinked organopolysiloxane polymer having a hydrophilic group. The hydrophilic group is preferably a polyether group and a polyglycerin group. The crosslinked organopolysiloxane polymer having a polyether group and/or a polyglycerin group can be obtained by reaction of alkylhydrogenpolysiloxane and a crosslinking agent that has a reactive vinyl type unsaturated group(s) at the terminal of the molecular chain. Illustrative examples of the alkylhydrogenpolysiloxane include methylhydrogenpolysiloxane in which a polyoxyethylene chain is grafted, methylhydrogenpolysiloxane in which a polyglycerin chain is grafted, etc., and the molecule has to contain two or more hydrogen atoms that are bonded to silicon atom(s). This crosslinked organopolysiloxane polymer is swollen with larger weight of low viscosity silicone with the viscosity of 0.65 to 100.0 mm$^2$/second (at 25° C.), hydrocarbon oil such as liquid paraffin, squalane, and isododecane, glyceride oil such as trioctanoin, and/or ester oil. The crosslinking agent is exemplified by a molecule having two or more vinyl type reaction moieties such as methylvinylpolysiloxane, α,ω-alkenyldiene, glycerin triallyl ether, polyoxyalkynylated glycerin triallyl ether, trimethylolpropane triallyl ether, and polyoxyalkynylated trimethylolpropane triallyl ether, provided that the crosslinked product by the reaction thereof contains at least one hydrophilic group. Preferable examples of the composition include the ones described in JP 2631772B, JP H09-136813A1, JP 2001-342255A1, WO 03/20828A1, and JP 2009-185296A. Illustrative examples of the commercially products of these crosslinked organopolysiloxane include KSG-210, KSG-240, and KSG-710, which are pastes mixed with silicone oil; KSG-310, KSG-320, KSG-330, KSG-340, KSG-820, KSG-830, and KSG-840, which are pastes mixed with hydrocarbon oil or triglyceride oil (all of which are manufactured by Shin-Etsu Chemical Co., Ltd.), but not particularly limited thereto. The composition composed of liquid oil and crosslinked organopolysiloxane having a hydrophilic group(s) is preferably blended in an amount of 0.1 to 50 mass %, more preferably 1 to 30 mass % relative to the whole amount of the cosmetic.

In the present invention, silicone wax may be contained in accordance with the object. This silicone wax is preferably polylactone-modified polysiloxane having bonded polylactone, which is a ring opening polymerization product of a lactone compound having a ring of five or more atoms. Alternatively, this silicone wax is preferably acrylic-modified polysiloxane with the molecule containing at least one functional group selected from a pyrrolidone group, a long-chain alkyl group, a polyoxyalkylene group, a fluoroalkyl group, and anionic groups such as a carboxy group. Illustrative examples of commercial products thereof include KP-561P and KP-562P (all of which are manufactured by Shin-Etsu Chemical Co., Ltd.) as wax having a ling-chain alkyl group.

The inventive cosmetic may further contain a component(s) used for ordinary cosmetics, an oil-soluble gelation agent (organic-modified clay mineral), etc.

Illustrative examples of the oil-soluble gelation agent include one or two or more kinds of oil-soluble gelation agent(s) selected from metal soap such as aluminum stearate, magnesium stearate, and zinc myristate; an amino acid derivative such as N-lauroyl-L-glutamic acid and α,γ-di-n-butyl amine; dextrin fatty acid ester such as dextrin palmitate ester, dextrin stearate ester, and dextrin 2-ethylhexanoate palmitate ester; sucrose fatty acid ester such as sucrose palmitate ester and sucrose stearate ester; fructo-oligosaccharide fatty acid ester such as fructo-oligosaccharide stearate ester and fructo-oligosaccharide 2-ethylhexanoate ester; a benzylidene derivative of sorbitol such as monobenzylidene sorbitol and dibenzylidene sorbitol; an organic-modified clay mineral such as dimethyl benzyl dodecyl ammonium montomorillonite clay and dimethyl dioctadecyl ammonium montomorillonite clay.

The inventive cosmetic includes cosmetics in which the cosmetic component(s) described above are blended, such as make-up cosmetics including make-up foundation, concealer, white powder, liquid foundation, oil foundation, rouge, eye shadow, mascara, eye liner, eye blow, and a lipstick; hair cosmetics including shampoo, rinse, treatment, and setting material; UV-protective cosmetics including antiperspirant, sunscreen oil, sunscreen lotion, and sunscreen cream.

These cosmetics may be in various forms, such as liquid, emulsion, cream, solid, paste, gel, powder, pressed, laminated, mousse, spray, and stick forms.

These cosmetics may be in various types, such as a water-base, an oil-base, a water-in-oil emulsion, an oil-in-water emulsion, a non-aqueous emulsion, a multi-emulsion including W/O/W and O/W/O.

EXAMPLE

Hereinafter, the present invention will be described specifically by showing Synthesis Examples, together with Examples of the inventive cosmetic and Comparative Examples, but the present invention is not limited to the following Examples. Incidentally, "%" described below means "mass %" and represents the content of each component in mass % letting the total mass in each Example be 100% unless otherwise specifically noted. The viscosity is a value at 25° C.

Synthesis Examples (1) to (5), Comparative Synthesis Examples (1) to (4)

Into a glass flask equipped with a stirrer, a thermometer, and a reflux condenser, 140.0 g of methyl ethyl ketone, each monomer shown in Table 1 below, and 4.0 g of t-butylperoxy-2-ethylhexanoate were introduced, and this was heated to reflux while stirring under a nitrogen flow. After 5 hours of polymerization, the volatile components were evaporated under reduced pressure to give each silicone copolymer (Synthesis Examples (1) to (5) and Comparative Synthesis Examples (1) to (4)). Each weight average molecular weight was determined by GPC (in terms of polystyrene), and each refractive index was determined with Abbe's refractometer (25° C.). The obtained polymer and isododecane were mixed in a mass ratio of 7:3 and dissolved by heating to 120° C., followed by cooling to 25° C. Then, the appearance was observed and represented as "good" in case of transparent (slightly cloudy) dissolution or "bad" in case of precipitation of the resin (the silicone copolymer).

TABLE 1

|  | Synthesis Examples of acryl silicone copolymer (g) | | | | | Comparative Synthesis Examples of acryl silicone copolymer (g) | | | |
| --- | --- | --- | --- | --- | --- | --- | --- | --- | --- |
|  | (1) | (2) | (3) | (4) | (5) | (1) | (2) | (3) | (4) |
| Silicone macromonomer (1) | 50 | | | 65 | | | | | |
| Silicone macromonomer (2) | | 60 | | | | | | | |
| Silicone macromonomer (3) | | | 35 | | | | | | |
| Silicone macromonomer (4) | | | | | | 50 | | | |
| Silicone macromonomer (5) | | | | | | | | 35 | |
| Silicone macromonomer (6) | | | | | | | 65 | | 30 |
| Silicone macromonomer (7) | | | | | 70 | | | | |
| Adamantyl methacrylate | | 30 | | | | | | | |
| Isobornyl methacrylate | | | | 35 | 30 | | 35 | | |
| Dicyclopentenyl methacrylate | 50 | | 35 | | | 50 | | 35 | |
| Methyl methacrylate | | 10 | | | | | | | 23 |
| Stearyl methacrylate | | | 30 | | | | | 30 | 25 |
| 2-Hydroxyethyl methacrylate | | | | | | | | | 22 |
| Refractive index (ATAGO) | 1.50 | 1.51 | 1.52 | 1.48 | 1.47 | 1.44 | 1.45 | 1.45 | 1.44 |
| Weight average molecular weight by GPC (TOSOH CORP. in terms of polystyrene) | 60000 | 140000 | 80000 | 85000 | 55000 | 56000 | 75000 | 80000 | 41000 |
| Solubility to isododecane | good | good | good | good | good | good | good | good | bad |

TABLE 1-continued

|  | Synthesis Examples of acryl silicone copolymer (g) | | | | | Comparative Synthesis Examples of acryl silicone copolymer (g) | | | |
| --- | --- | --- | --- | --- | --- | --- | --- | --- | --- |
|  | (1) | (2) | (3) | (4) | (5) | (1) | (2) | (3) | (4) |

Silicone macromonomer (1):
$$H_2C=C(CH_3)-C(=O)-O-C_3H_6-[Si(CH_3)_2-O]_{10}-[Si(Ph)_2-O]_5-Si(CH_3)_2-CH_3$$

Silicone macromonomer (2):
$$H_2C=C(CH_3)-C(=O)-O-C_3H_6-[Si(CH_3)_2-O]_{80}-[Si(Ph)_2-O]_{40}-Si(CH_3)_2-CH_3$$

Silicone macromonomer (3):
$$H_2C=C(CH_3)-C(=O)-O-C_3H_6-[Si(CH_3)_2-O]_{10}-[Si(Ph)_2-O]_{20}-Si(CH_3)_2-n\text{-}Bu$$

Silicone macromonomer (4) for comparison:
$$H_2C=C(CH_3)-C(=O)-O-C_3H_6-[Si(CH_3)_2-O]_{15}-Si(CH_3)_2-n\text{-}Bu$$

Silicone macromonomer (5) for comparison:
$$H_2C=C(CH_3)-C(=O)-O-C_3H_6-[Si(CH_3)_2-O]_{30}-Si(CH_3)_2-CH_3$$

Silicone macromonomer (6) for comparison:
$$H_2C=C(CH_3)-C(=O)-O-C_3H_6-[Si(CH_3)_2-O]_{10}-[Si(Ph)_2-O]_2-Si(CH_3)_2-CH_3$$

Silicone macromonomer (7):
$$H_2C=C(CH_3)-C(=O)-O-C_3H_6-[Si(CH_3)_2-O]_{12}-[Si(Ph)_2-O]_3-Si(CH_3)_2-CH_3$$

Examples 1 to 6 and Comparative Examples 1 to 4

(Evaluation 1)

A lipstick was produced in accordance with each composition shown in Table 2, and the usability was evaluated.

[Method for Sensory Evaluation]

Each lipstick shown in Table 2 was applied to lips sufficiently, dried, and then evaluated. This was subjected to sensory evaluation of gloss (shine), nonstick feeling, cosmetic sustainability (secondary adhesion), adherence, and feeling of free from stiffness. These results were represented by the following criteria based on the number of panelist who answered that "it was effective".

[Evaluation Criteria]

Exc. (excellent): 4 to 5 people answered that "it was effective"

Good: 3 people answered that "it was effective"

Fair: 2 people answered that "it was effective"

Bad: 0 or 1 people answered that "it was effective"

[Production Method]

Step A: Components 1 to 18 and 20 were mixed with heating.

Step B: Components 21 to 25 were mixed homogeneously.

Step C: B was added to A, Component 19 was added thereto, and this was homogenized.

TABLE 2

|   | Components | Examples 1 | 2 | 3 | 4 | 5 | 6 | Comparative Examples 1 | 2 | 3 | 4 |
|---|---|---|---|---|---|---|---|---|---|---|---|
| 1 | Copolymer of Synthesis Example (1) | 10 | | | | | | | | | |
| 2 | Copolymer of Synthesis Example (2) | | 8 | | | | | | | | |
| 3 | Copolymer of Synthesis Example (3) | | | 15 | | 5 | | | | | |
| 4 | Copolymer of Synthesis Example (4) | | | | 10 | | | | | | |
| 5 | Copolymer of Synthesis Example (5) | | | | | | 10 | | | | |
| 6 | Copolymer of Comparative Synthesis Example (1) | | | | | | | 10 | | | |
| 7 | Copolymer of Comparative Synthesis Example (2) | | | | | | | | 10 | | |
| 8 | Copolymer of Comparative Synthesis Example (3) | | | | | | | | | 15 | |
| 9 | Copolymer of Comparative Synthesis Example (4) | | | | | | | | | | 10 |
| 10 | Candellila wax | 13 | 13 | 13 | 13 | 13 | 13 | 13 | 13 | 13 | 13 |
| 11 | Microcrystalline wax | 5 | 10 | 5 | 5 | 7 | 5 | 5 | 5 | 5 | 5 |
| 12 | Ceresin wax | 10 | 10 | 10 | 10 | 10 | 10 | 10 | 10 | 10 | 10 |
| 13 | Isododecane | 15 | | 10 | 15 | 10 | 15 | 15 | 15 | 10 | 15 |
| 14 | Decamethylcyclopentasiloxane | | 17 | | | 5 | | | | | |
| 15 | Isotridecyl isononanoate | 15 | 15 | 15 | 15 | 15 | 15 | 15 | 15 | 15 | 15 |
| 16 | Hydrogenated polyisobutene | 15 | 12 | 15 | 15 | 15 | 15 | 15 | 15 | 15 | 15 |
| 17 | Diisostearyl malate | 12 | 12 | 12 | 12 | 15 | 12 | 12 | 12 | 12 | 12 |
| 18 | Alkylpolyglycerin-modified silicone (*1) | 0.5 | 0.5 | 0.5 | 0.5 | 0.5 | 0.5 | 0.5 | 0.5 | 0.5 | 0.5 |
| 19 | Fragrance | appropriate | appropriate | appropriate | appropriate | appropriate | appropriate | appropriate | appropriate | appropriate | appropriate |
| 20 | Antiseptics | appropriate | appropriate | appropriate | appropriate | appropriate | appropriate | appropriate | appropriate | appropriate | appropriate |
| 21 | Silicone-treated red 202 (*2) | 0.8 | 0.8 | 0.8 | 0.8 | 0.8 | 0.8 | 0.8 | 0.8 | 0.8 | 0.8 |
| 22 | Silicone-treated Bengal red (*2) | 1.5 | 1.5 | 1.5 | 1.5 | 1.5 | 1.5 | 1.5 | 1.5 | 1.5 | 1.5 |
| 23 | Silicone-treated yellow iron oxide (*2) | 1 | 1 | 1 | 1 | 1 | 1 | 1 | 1 | 1 | 1 |
| 24 | Silicone-treated black iron oxide (*2) | 0.2 | 0.2 | 0.2 | 0.2 | 0.2 | 0.2 | 0.2 | 0.2 | 0.2 | 0.2 |
| 25 | Silicone-treated titanium oxide (*2) | 1 | 1 | 1 | 1 | 1 | 1 | 1 | 1 | 1 | 1 |
| Evaluation | Gloss | Exc. | Exc. | Exc. | Good | Good | Good | Bad | Bad | Fair | Bad |
| | nonstick feeling | Exc. | Good | Exc. | Good | Exc. | Exc. | Good | Bad | Fair | Fair |
| | cosmetic sustainability | Exc. | Good | Exc. | Exc. | Exc. | Good | Fair | Bad | Good | Good |
| | adherence | Exc. | Exc. | Good | Good | Fair | Fair | Fair | Fair | Fair | Fair |
| | free from stiffness | Exc. | Exc. | Exc. | Exc. | Good | Good | Fair | Fair | Bad | Bad |

(*1) KF-6105 manufactured by Shin-Etsu Chemical Co., Ltd.
(*2) treated with KF-9909 manufactured by Shin-Etsu Chemical Co., Ltd.

As shown by the results in Tables 1 and 2 described above, it was confirmed that each make-up cosmetic according to the present invention successfully combined gloss (shine), nonstick feeling, good cosmetic sustainability (secondary adhesion), good adherence, and feeling of free from stiffness. On the other hand, each make-up cosmetic of Comparative Examples 1 to 4, using a copolymer in which the ratio of content of phenyl group was out of the specific of the present invention (n/m=5) or a copolymer without containing a phenyl group, lacked gloss and showed unsatisfactory results in other evaluations. As shown in Table 1, each copolymer of Synthesis Examples (1) to (5), in which an aliphatic (meth)acrylic monomer was used as a monomer of acryl silicone copolymer in addition to the silicone macromonomer shown by the general formula (1), showed good solubility to isododecane, which is a volatile organic oil.

Example 7

Nail Enamel

| Composition | mass % |
|---|---|
| 1. Copolymer of Synthesis Example (2) dissolved in isododecane (30 mass %) | 45.0 |
| 2. Methyltrimethicone (*3) | 5.0 |

-continued

| Composition | mass % |
|---|---|
| 3. Nitrocellulose | 3.0 |
| 4. Camphor | 0.5 |
| 5. Acetyltributyl citrate | 1.0 |
| 6. Dimethyldistearylammonium hectorite | 0.5 |
| 7. Butyl acetate | 30.0 |
| 8. Ethyl acetate | 10.0 |
| 9. Isopropyl alcohol | 5.0 |
| 10. Coloring pigment | appropriate |
| Total | 100.0 |

(*3) TMF-1.5 manufactured by Shin-Etsu Chemical Co., Ltd.

Comparative Example 5

Nail Enamel

| Composition | mass % |
|---|---|
| 1. Copolymer of Comparative Synthesis Example (4) dissolved in isododecane (30 mass %) | 45.0 |
| 2. Methyltrimethicone (*3) | 5.0 |
| 3. Nitrocellulose | 3.0 |
| 4. Camphor | 0.5 |
| 5. Acetyltributyl citrate | 1.0 |
| 6. Dimethyldistearylammonium hectorite | 0.5 |

-continued

| Composition | mass % |
|---|---|
| 7. Butyl acetate | 30.0 |
| 8. Ethyl acetate | 10.0 |
| 9. Isopropyl alcohol | 5.0 |
| 10. Coloring pigment | appropriate |
| Total | 100.0 |

(*3) TMF-1.5 manufactured by Shin-Etsu Chemical Co., Ltd.

<Preparation of Nail Enamel>
A: Components 7 to 9 were mixed, and components 4 to 6 were added thereto, followed by mixing homogeneously.
B: Components 1 to 3 were added to A and mixed.
C: Component 10 was added to B to give nail enamel.

According to evaluations by specialist, it was confirmed that the nail enamel of Example 7 obtained as described above was superior in spreading lightly, giving gloss to nails, and having nonstick feeling and sustainability compared to the nail enamel of Comparative Example 5.

Example 8

Mascara

| Composition | mass % |
|---|---|
| 1. Copolymer of Synthesis Example (3) | 6.0 |
| 2. Branched polyether-modified silicone (*4) | 2.0 |
| 3. Organic-modified clay mineral (*5) | 5.0 |
| 4. Carnauba wax | 7.0 |
| 5. Bees wax | 6.0 |
| 6. Isododecane | 64.0 |
| 7. Silicone-treated black iron oxide (*6) | 5.0 |
| 8. Silicone-treated talc (*6) | 5.0 |
| 9. Antiseptic | appropriate |
| Total | 100.0 |

(*4) KF-6028P manufactured by Shin-Etsu Chemical Co., Ltd.
(*5) BENTON 38VCG manufactured by Elementis Specialities
(*6) treated with KF-9909 manufactured by Shin-Etsu Chemical Co., Ltd.

Comparative Example 6

Mascara

| Composition | mass % |
|---|---|
| 1. Copolymer of Comparative Synthesis Example (3) | 6.0 |
| 2. Branched polyether-modified silicone (*4) | 2.0 |
| 3. Organic-modified clay mineral (*5) | 5.0 |
| 4. Carnauba wax | 7.0 |
| 5. Bees wax | 6.0 |
| 6. Isododecane | 64.0 |
| 7. Silicone-treated black iron oxide (*6) | 5.0 |
| 8. Silicone-treated talc (*6) | 5.0 |
| 9. Antiseptic | appropriate |
| Total | 100.0 |

(*4) KF-6028P manufactured by Shin-Etsu Chemical Co., Ltd.
(*5) BENTON 38VCG manufactured by Elementis Specialities
(*6) treated with KF-9909 manufactured by Shin-Etsu Chemical Co., Ltd.

<Preparation of Mascara>
Components 1 to 9 were mixed homogeneously while heating to give mascara.

According to evaluations by specialist, it was confirmed that the mascara of Example 8 obtained as described above showed gloss, better spreading, a voluminous feeling, and cosmetic sustainability compared to the mascara of Comparative Example 6.

Example 9

Sun-Cut Cream

| Composition | mass % |
|---|---|
| 1. Decamethylcyclopentasiloxane | 17.5 |
| 2. Copolymer of Synthesis Example (1) | 12.0 |
| 3. Glyceryl triisooctanoate | 5.0 |
| 4. Octyl paramethoxycinnamate | 6.0 |
| 5. Crosslinked polyether-modified silicone (*7) | 5.0 |
| 6. Polyether-modified silicone (*8) | 1.0 |
| 7. Oleophilic-treated zinc oxide | 20.0 |
| 8. Sodium chloride | 0.5 |
| 9. 1,3-Butylene glycol | 2.0 |
| 10. Antiseptic | appropriate |
| 11. Fragrance | appropriate |
| 12. Purified water | 31.0 |
| Total | 100.0 |

(*7) Crosslinked polyether-modified silicone: KSG210 manufactured by Shin-Etsu Chemical Co., Ltd.
(*8) Polyether-modified silicone: KF-6017 manufactured by Shin-Etsu Chemical Co., Ltd.

(Production Method)
A: Component 2 was added to part of component 1 and homogenized. Component 7 was added thereto and dispersed with a beads mill.
B: The remainder of component 1 and components 3 to 6 were mixed homogeneously.
C: Components 8 to 10 and component 12 were mixed to be dissolved homogeneously with each other.
D: C was added to B to be emulsified, and A and component 11 were added thereto to give sun-cut cream.

It was confirmed that the sun-cut cream obtained as described above was glossy, free from sticky touch, lightly spreadable, superior in adherence to be set favorably, and particularly excellent in cosmetic sustainability to be very stable with temperature or time.

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:
1. A cosmetic comprising
an acryl silicone copolymer that has a refractive index of 1.47 or more, the acryl silicone copolymer having
a (meth)acrylic chain in a main chain and
a structure containing at least a silicone macromonomer shown by the following general formula (1) as a monomer unit:

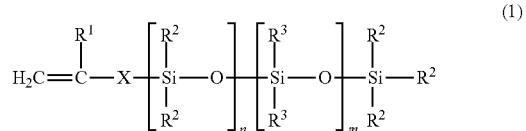

(1)

wherein in the formula (1),

X represents —COOR$^4$—, where R$^4$ represents a divalent aliphatic group;

R$^1$ represents a hydrogen atom or a methyl group;

each R$^2$ represents the same or different unsubstituted monovalent alkyl group having 1 to 6 carbon atoms;

R$^3$ represents a phenyl group;

n is an integer of 1 to 100, m is an integer of 1 to 100, and a component ratio n/m is in a range of from 1/2 to 4/1.

2. The cosmetic according to claim 1, wherein the acryl silicone copolymer contains an alicyclic (meth)acrylic monomer as a monomer unit.

3. The cosmetic according to claim 2, wherein the acryl silicone copolymer contains 30 to 70 mass % of the silicone macromonomer shown by the general formula (1) as a monomer unit and 30 to 70 mass % of the alicyclic (meth)acrylic monomer as a monomer unit.

4. The cosmetic according to claim 1, wherein the acryl silicone copolymer does not precipitate or separate at 25° C. from a mixture of the acryl silicone copolymer with a volatile silicone oil or a volatile organic oil in a mass ratio of 7:3.

5. The cosmetic according to claim 2, wherein the acryl silicone copolymer does not precipitate or separate at 25° C. from a mixture of the acryl silicone copolymer with a volatile silicone oil or a volatile organic oil in a mass ratio of 7:3.

6. The cosmetic according to claim 3, wherein the acryl silicone copolymer does not precipitate or separate at 25° C. from a mixture of the acryl silicone copolymer with a volatile silicone oil or a volatile organic oil in a mass ratio of 7:3.

7. The cosmetic according to claim 1, further comprising a volatile silicone oil or a volatile organic oil in addition to the acryl silicone copolymer.

8. The cosmetic according to claim 2, further comprising a volatile silicone oil or a volatile organic oil in addition to the acryl silicone copolymer.

9. The cosmetic according to claim 3, further comprising a volatile silicone oil or a volatile organic oil in addition to the acryl silicone copolymer.

10. The cosmetic according to claim 4, further comprising a volatile silicone oil or a volatile organic oil in addition to the acryl silicone copolymer.

11. The cosmetic according to claim 5, further comprising a volatile silicone oil or a volatile organic oil in addition to the acryl silicone copolymer.

12. The cosmetic according to claim 6, further comprising a volatile silicone oil or a volatile organic oil in addition to the acryl silicone copolymer.

13. The cosmetic according to claim 1, wherein the cosmetic is a make-up cosmetic.

14. The cosmetic according to claim 2, wherein the cosmetic is a make-up cosmetic.

15. The cosmetic according to claim 3, wherein the cosmetic is a make-up cosmetic.

16. The cosmetic according to claim 4, wherein the cosmetic is a make-up cosmetic.

17. The cosmetic according to claim 7, wherein the cosmetic is a make-up cosmetic.

18. The cosmetic according to claim 1, wherein the acryl silicone copolymer has a refractive index in a range of 1.47 to 1.54.

* * * * *